US011744989B2

(12) United States Patent
Blacker

(10) Patent No.: US 11,744,989 B2
(45) Date of Patent: Sep. 5, 2023

(54) SYSTEM FOR GUIDE CATHETER CONTROL WITH INTRODUCER CONNECTOR

(71) Applicant: Corindus, Inc., Waltham, MA (US)

(72) Inventor: Steven J. Blacker, Framingham, MA (US)

(73) Assignee: Corindus, Inc., Newton, MA (US)

(*) Notice: Subject to any disclaimer, the term of this patent is extended or adjusted under 35 U.S.C. 154(b) by 319 days.

(21) Appl. No.: 17/077,779

(22) Filed: Oct. 22, 2020

(65) Prior Publication Data

US 2021/0100980 A1 Apr. 8, 2021

Related U.S. Application Data

(60) Continuation of application No. 15/953,971, filed on Apr. 16, 2018, now Pat. No. 10,828,463, which is a continuation of application No. 15/229,338, filed on Aug. 5, 2016, now Pat. No. 9,993,615, which is a division of application No. 14/106,638, filed on Dec. 13, 2013, now Pat. No. 9,427,562.

(60) Provisional application No. 61/737,092, filed on Dec. 13, 2012.

(51) Int. Cl.
| | |
|---|---|
| *A61M 25/01* | (2006.01) |
| *A61M 39/10* | (2006.01) |
| *A61B 17/34* | (2006.01) |
| *A61B 34/30* | (2016.01) |
| *A61B 34/20* | (2016.01) |
| *A61B 6/00* | (2006.01) |
| *A61M 39/06* | (2006.01) |

(52) U.S. Cl.
CPC .......... *A61M 25/0113* (2013.01); *A61B 6/48* (2013.01); *A61B 17/3415* (2013.01); *A61B 17/3498* (2013.01); *A61B 34/20* (2016.02); *A61B 34/30* (2016.02); *A61M 39/06* (2013.01); *A61M 39/10* (2013.01); *A61M 39/1055* (2013.01); *A61B 2034/2065* (2016.02); *A61B 2034/301* (2016.02); *A61M 2039/062* (2013.01)

(58) Field of Classification Search
CPC ........ A61B 17/3498; A61B 2019/2211; A61B 2034/301; A61B 34/30; A61M 25/0113; A61M 39/10; A61M 2039/1061
See application file for complete search history.

(56) References Cited

U.S. PATENT DOCUMENTS

| | | | |
|---|---|---|---|
| 3,825,001 A * | 7/1974 | Bennet | A61M 25/0111 604/170.02 |
| 5,735,271 A | 4/1998 | Lorenzen et al. | |
| 8,708,952 B2 | 4/2014 | Cohen et al. | |
| (Continued) | | | |

OTHER PUBLICATIONS

Extended European Search Report for EP 13835435.2; dated Sep. 21, 2016; 8 pages.

*Primary Examiner* — Deanna K Hall

(57) ABSTRACT

An introducer assembly for introducing a catheter into a patient, includes a sheath having a distal end and a proximal end with a hollow lumen extending between the distal end and proximal end. The assembly also includes a coupler having a distal end operatively coupled to the proximal end of the sheath, the coupler having an internal passage in fluid communication with the hollow lumen. The assembly further includes a connector having a distal end operatively coupled to the coupler proximate the distal end of the coupler.

14 Claims, 14 Drawing Sheets

(56) References Cited

U.S. PATENT DOCUMENTS

| | | | |
|---|---|---|---|
| 10,258,285 B2 * | 4/2019 | Hauck ................. | A61B 5/6885 |
| 2008/0051820 A1 | 2/2008 | Gong et al. | |
| 2008/0300592 A1 | 12/2008 | Weitzner et al. | |
| 2010/0036329 A1 | 2/2010 | Razack | |
| 2012/0179032 A1 | 7/2012 | Bromander et al. | |

* cited by examiner

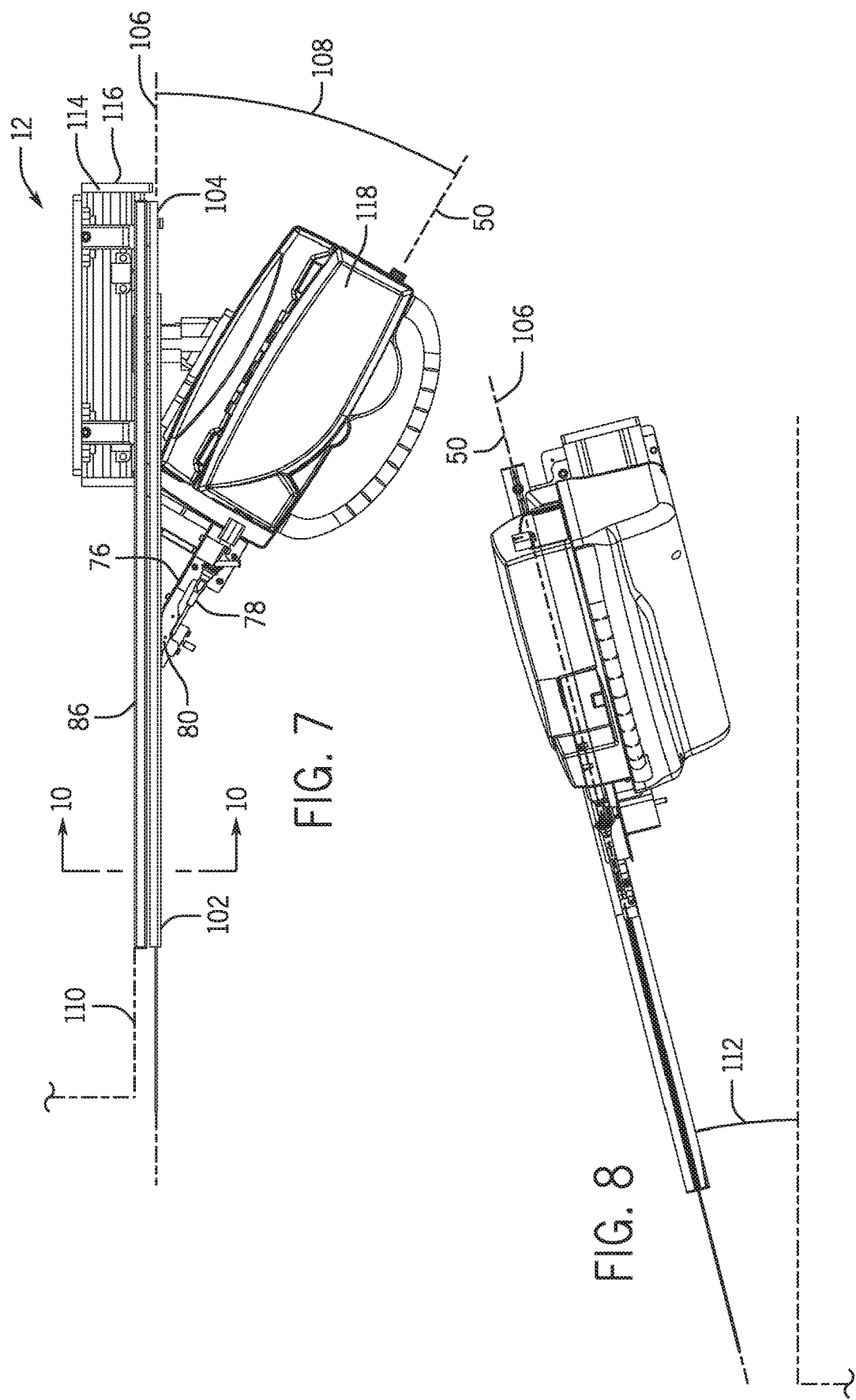

SYSTEM FOR GUIDE CATHETER CONTROL WITH INTRODUCER CONNECTOR

CROSS-REFERENCE TO RELATED PATENT APPLICATIONS

This application is a continuation application of U.S. patent application Ser. No. 15/953,971, filed Apr. 16, 2018, entitled SYSTEM FOR GUIDE CATHETER CONTROL WITH INTRODUCER CONNECTOR, which is a continuation application of U.S. patent application Ser. No. 15/229,338, filed Aug. 5, 2016, entitled SYSTEM FOR GUIDE CATHETER CONTROL WITH INTRODUCER CONNECTOR, now U.S. Pat. No. 9,993,615, which is a divisional application of U.S. patent application Ser. No. 14/106,638, filed Dec. 13, 2013, entitled SYSTEM FOR GUIDE CATHETER CONTROL WITH INTRODUCER CONNECTOR, now U.S. Pat. No. 9,426,562, which claims priority to U.S. Provisional Application No. 61/737,092, filed Dec. 13, 2012, entitled SYSTEM FOR GUIDE CATHETER CONTROL WITH INTRODUCER CONNECTOR, all of which are incorporated herein by reference in their entirety.

BACKGROUND

The present invention relates generally to the field of catheter systems for performing diagnostic and/or intervention procedures. The present invention relates specifically to a guide catheter control in robotic catheter system with an introducer connector.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery.

During one type of intervention procedure, a guide catheter is inserted into a patient's femoral artery through an introducer and positioned proximate the coronary ostium of a patient's heart. A guide wire is inserted into the guide catheter typically through a hemostasis valve and maneuvered through the patient's arterial system until the guide wire reaches the site of the lesion. A working catheter is then moved along the guide wire until the working catheter such as a balloon and stent are positioned proximate the lesion to open a blockage to allow for an increased flow of blood proximate the lesion. In addition to cardiovascular disease, other diseases may be treated with catheterization procedures.

SUMMARY OF THE INVENTION

In accordance with an embodiment, an introducer includes a coupler having a distal end configured to operatively couple a sheath and a connector extending from the proximal end of the coupler. The connector has a portion that expands and contracts along a longitudinal axis upon the application of a force applied to a distal end of the connector.

BRIEF DESCRIPTION OF THE DRAWINGS

FIG. 7 is a top view of the catheter bedside system of FIG. 2.
FIG. 8 is a side view of the catheter bedside system of FIG. 2.

DETAILED DESCRIPTION OF THE EXAMPLE EMBODIMENTS

Figure 1:
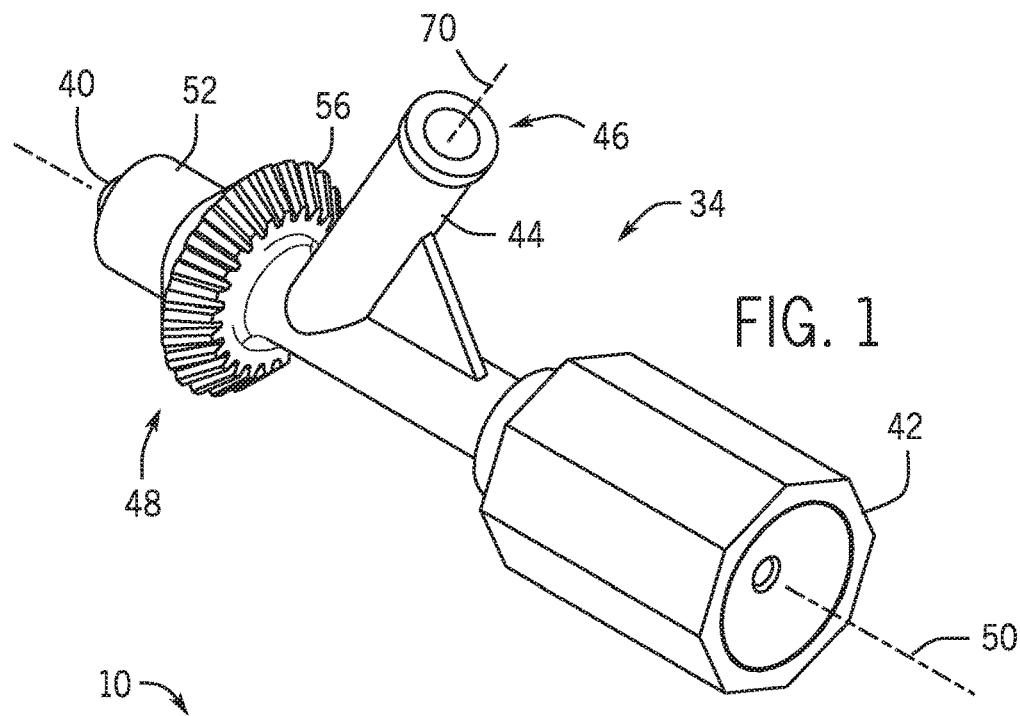
FIG. 1 is an isometric view of a hemostasis valve.

Referring to FIG. 1, a Y-connector or hemostasis valve 34 includes a valve body with a first leg 38 having a proximal port adjacent a proximal end 42 and a distal port adjacent a distal end 40. First leg 38 includes lumen extending between the proximal end 42 and the distal end 40. A valve 162 is disposed adjacent proximal end 42. A rotating luer connector 48 is rotatably secured to first leg 38 proximate distal end 40. Rotating luer connector 48 includes a member 56 configured to be rotatably driven by a drive mechanism of a robotic catheter system 10.

Figure 2:
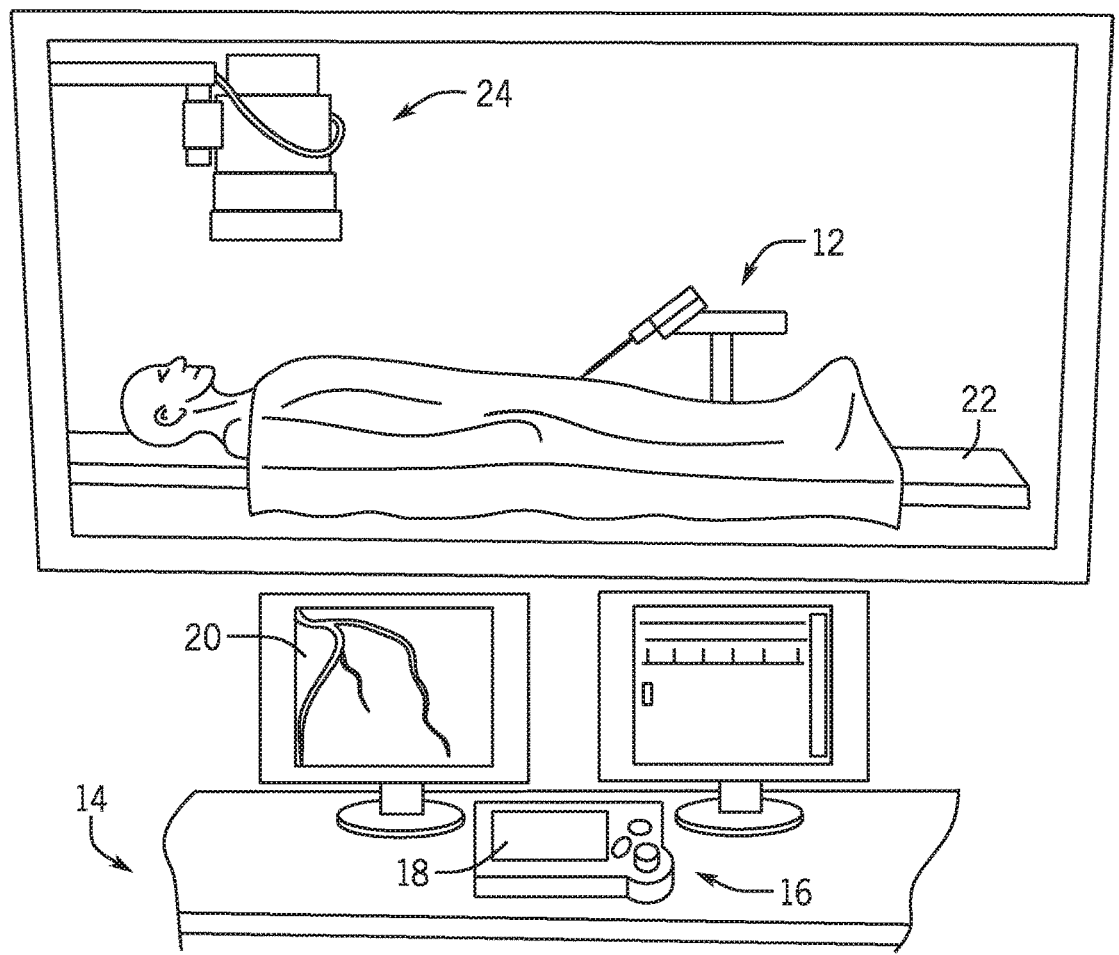
FIG. 2 is a schematic view of a robotic catheter control system.

Referring to FIG. 2, a robotic catheter system 10 includes a bedside system 12, a work station 14 including a controller 16, a user interface 18 and display 20. Bedside system 12 is located adjacent a patient bed 22 and an imaging system 24. Imaging system 24 may be any medical imaging system that may be used in conjunction with a catheter based medical procedure (e.g., non-digital x-ray, digital x-ray, CT, MRI, ultrasound, etc.).

In one embodiment, imaging system 24 is a digital x-ray imaging device that is in communication with workstation 14. Imaging system 24 is configured to take x-ray images of the appropriate area of patient during a particular procedure. For example, imaging system 24 may be configured to take one or more x-ray images of the heart to diagnose a heart condition. Imaging system 24 may also be configured to take one or more x-ray images during a catheter based medical procedure (e.g., real-time images) to assist the user of workstation 14 to properly position a guide wire, guide catheter, and a working catheter such as a stent during a procedure. The image or images may be displayed on display 20 to allow the user to accurately steer a distal tip of a guide wire or working catheter into proper position. As used herein the direction distal is used to refer to the direction closer to a patient in the intended use of the component and the term proximal is used to refer to the direction further away to a patient in the intended use of the component.

Figure 3:
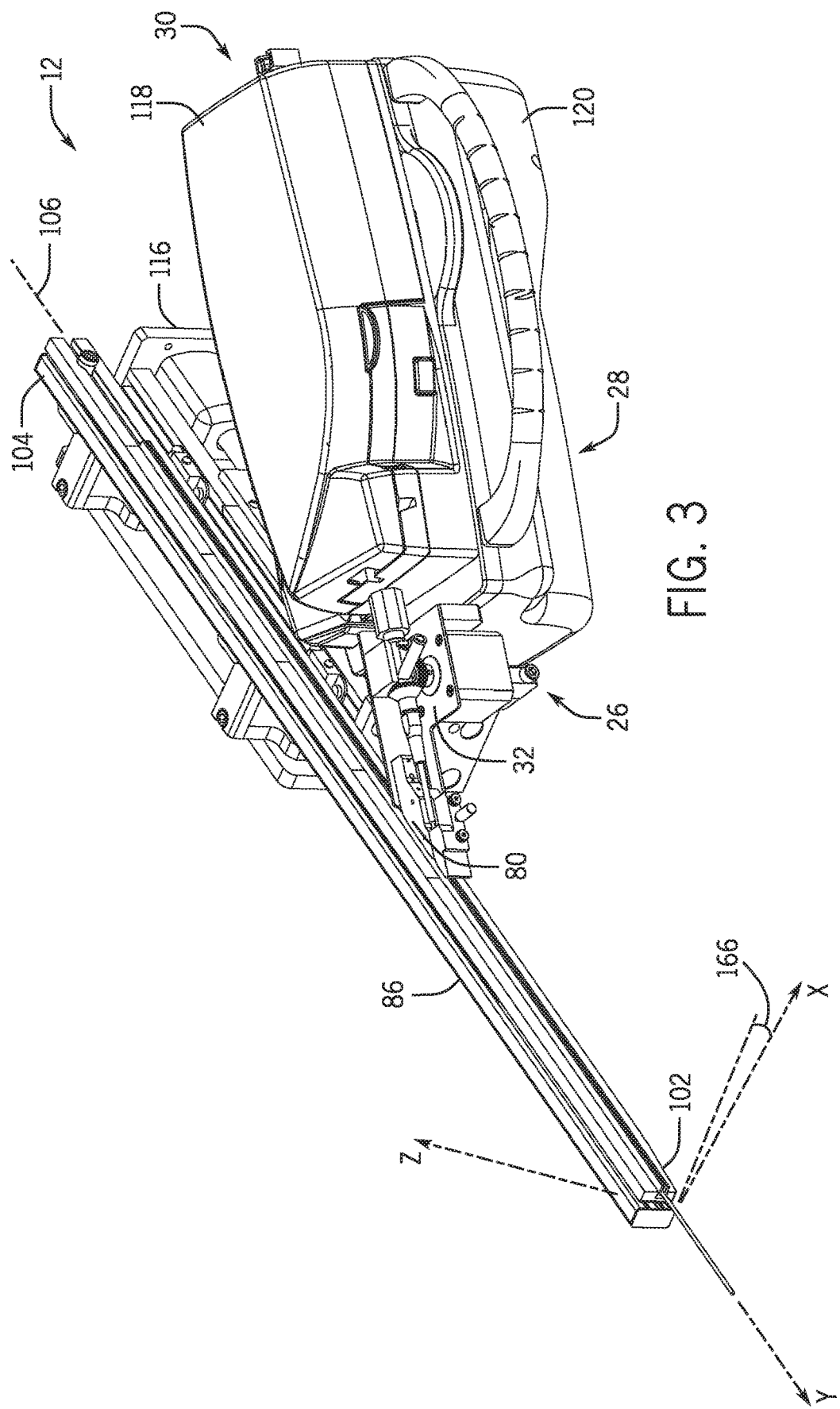
FIG. 3 is an isometric view of a catheter bedside system.

Referring to FIG. 3 bedside system 12 includes a guide catheter mechanism 26, a working catheter mechanism 28 and a guide wire mechanism 30. In one embodiment, working catheter mechanism 28 and guide wire mechanism 30 are of the type described in U.S. Pat. No. 7,887,549 entitled "Catheter System" which is incorporated herein in its entirety.

Figure 4:
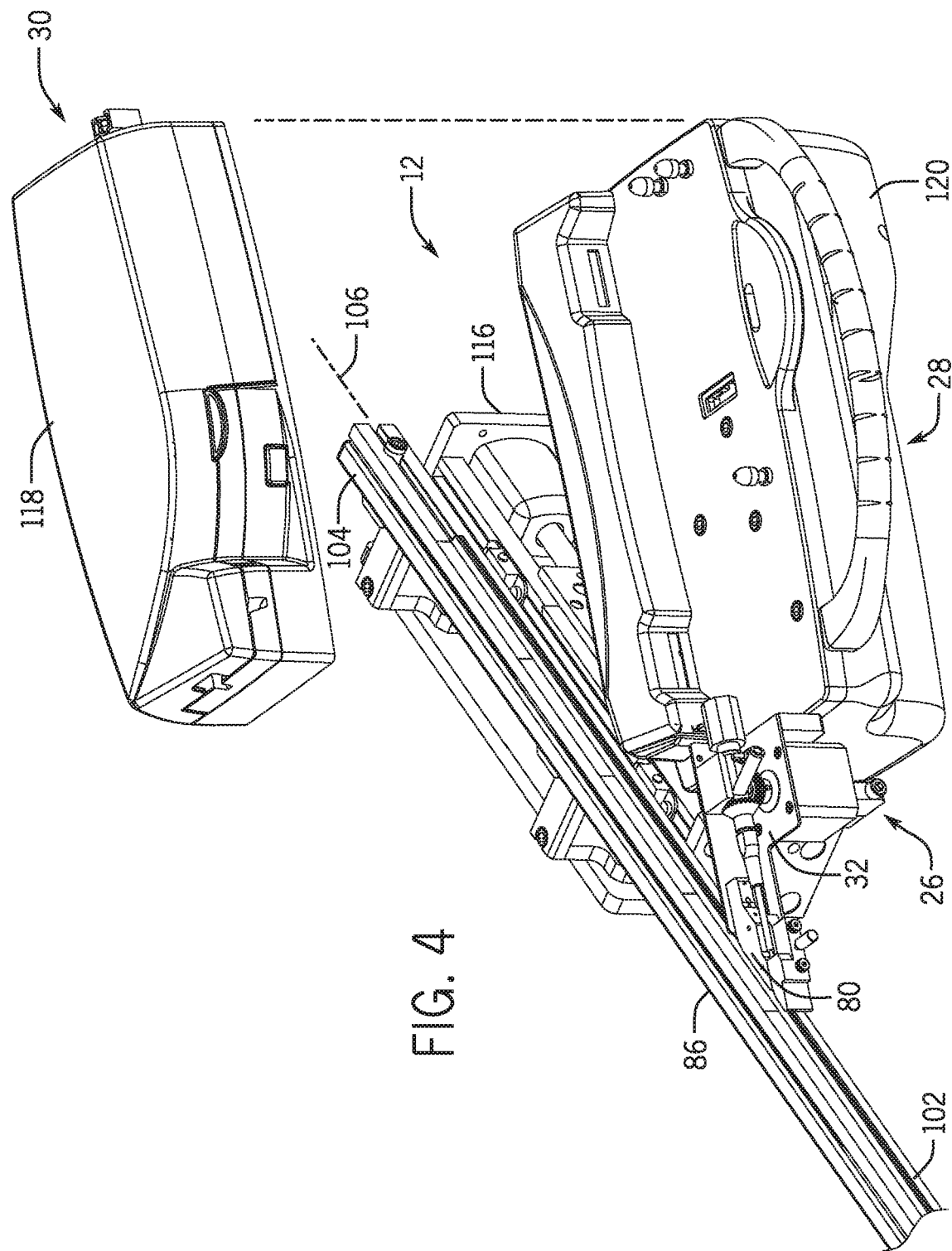
FIG. 4 is an isometric view of a catheter bedside system.
Figure 5:
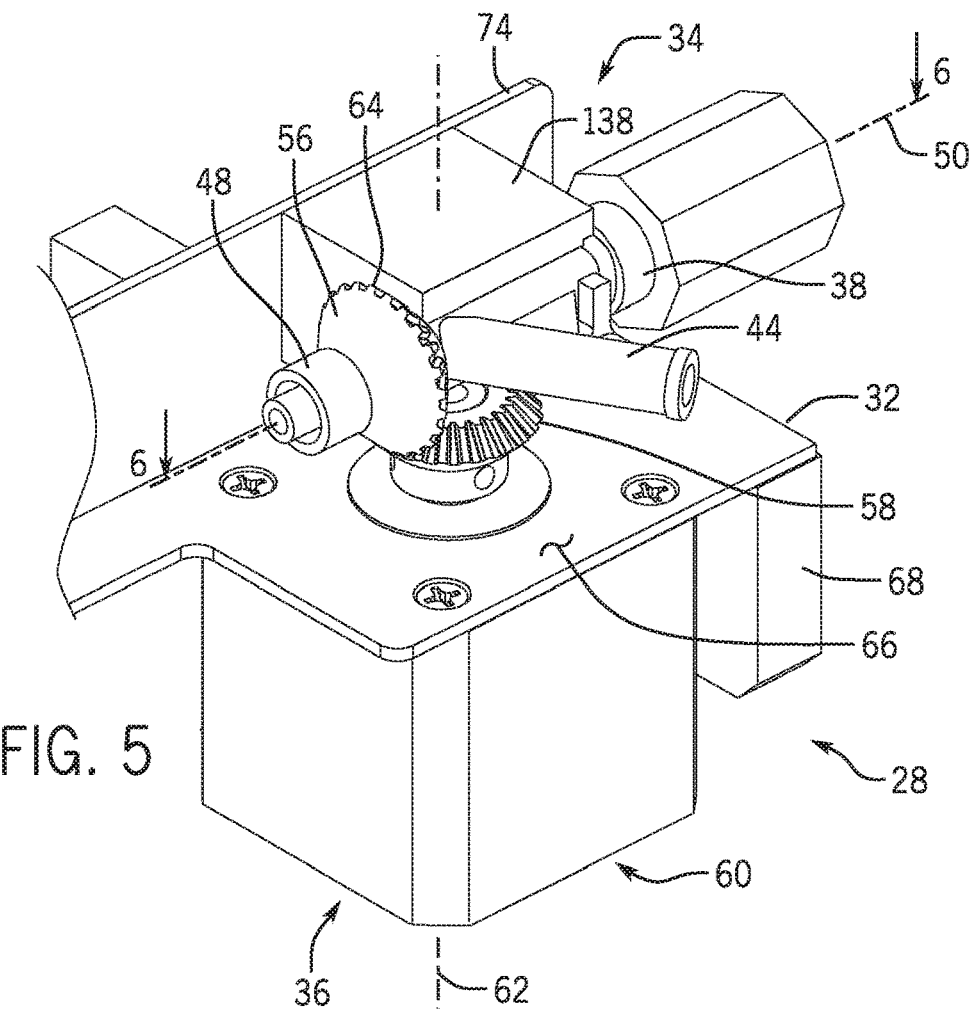
FIG. 5 is an isometric view of a hemostasis valve and guide catheter drive mechanism.

Referring to FIGS. 3-5 guide catheter mechanism 26 includes a base 32 configured to releasably receive a hemostasis valve 34 and a guide catheter rotational drive 36. Base 32 may include a quick release mechanism to releasably secure hemostasis valve 34 to base 32. One embodiment of a guide catheter quick release is disclosed in US application publication US 2012/0179032 entitled "Remote Catheter System With Steerable Catheter" which is incorporated herein in its entirety.

Hemostasis valve 34 includes a first leg 38 having a distal end 40 and a proximal end 42. A second leg 44 extends from first leg 38 and is in fluid communication with first leg 38 such that a fluid may be introduced into a proximate end 46 of second leg 44. Hemostasis valve first leg 38 defines a longitudinal axis 50 extending from proximal end 42 of first leg 38 to distal end 40 of first leg 38.

The distal end 40 of first leg 38 includes a rotating luer connector 48 that is rotatably coupled to distal end 40 of first leg 38. Rotating luer connector48 includes an external surface 52 and an internal region 54 having a luer female interface to releasably couple a guide catheter. Luer connectors are known in the art and provide a fluid tight connection between a guide catheter and a hemostasis valve. Luer connectors are covered by standards such as ISO 594 (including sections 594-1 and 594-2) and EN 1707.

In one embodiment external surface 52 of rotating luer connector 48 includes a gear 56 that is driven by rotational drive 36. Rotational drive 36 includes a drive gear 58 operatively connected to a motor 60. Gear 56 may be integrally formed with rotating luer connector 48 and coupled with a drive gear 58 for rotational movement of the rotating connector.

In another embodiment, gear 56 may be secured to the outer surface of rotational luer connector 48 such that gear 56 rotates along with the rotation of rotational luer connector 48 about longitudinal axis 50 of the first leg 38 of hemostasis valve 34.

Gears 56 and 58 may be beveled gears or miter gears to provide direct rotation of driven gear 56 from a shaft rotated by motor 60 and extending along an axis 62 perpendicular to longitudinal axis 50 of first leg 38 of hemostasis valve 34. Referring to FIG. 1, gear 56 is beveled such that gear teeth 64 extend in a direction toward proximal end 42 and away from distal end 40 of first leg 38. Additionally, in one embodiment driven gear 56 is located a distance from distal end 40 to permit attachment and removal of a guide catheter from rotational luer connector 48. Drive gear 58 is positioned below first leg 38 to permit easy removal of the hemostasis valve 34 from base 32.

Motor 60 may be secured to base 32, such that drive gear 58 is located above a first surface 66 of base 32 and motor 60 is located below an opposing second surface 68 of base 32. First surface 66 being closer to first leg 38 than second surface 68 of base 32.

Figure 6:
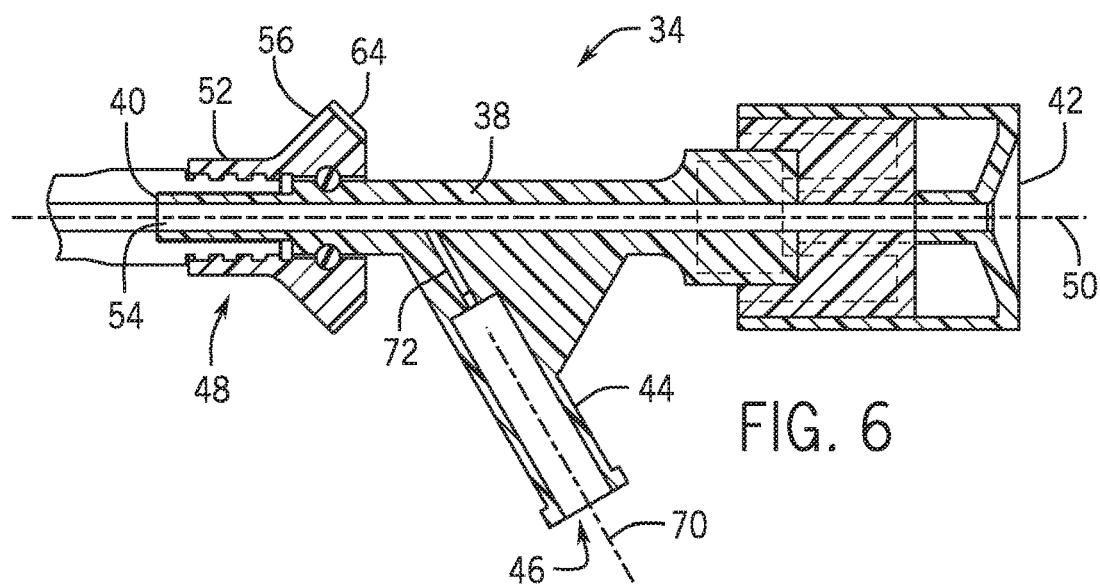
FIG. 6 is a cross-sectional view a hemostasis valve.

Referring to FIG. 1 FIG. 6 second leg 44 of hemostasis valve 34 has a longitudinal axis 70 extending longitudinally along second leg 44 from proximate end 46 to a distal end 72 adjacent first leg 38. A second leg working plane is defined by axis 50 of first leg 38 and axis 70 of second leg 44. In one embodiment hemostasis valve 34 is secured to base 32 such that the second leg working plane is not perpendicular to the horizontal as defined by gravity. Rather the second leg working plane forms an acute angle with respect to a vertical plane permitting an operator access to proximate end 46 of second leg 44. In one embodiment second leg working plane may be co-planer with a horizontal plane. As discussed above, hemostasis valve 34 may be releasably coupled to base 32 with a quick release that allows removal of hemostasis valve 34 from base 32.

Referring to FIG. 5, base 32 includes a raised wall 74 extending upwardly from and perpendicular to surface 66. Wall 74 extends in a direction parallel to axis 50 of hemostasis valve 34, when hemostasis valve 34 is secured to base 32. Wall 74 is proximate a rear portion 76 of base 32 and distal a front portion 78 of base 32. Gear 58 being intermediate wall 74 and front portion 78 of base 32. A guide member 80 is secured to wall 74 and extends in a direction substantially parallel to axis 50 when hemostasis valve 34 is secured to base 32. Guide member 80 has a guide portion 82 configured to direct a portion of a guide catheter prior to the guide catheter entering a sleeve 84.

Figure 10:
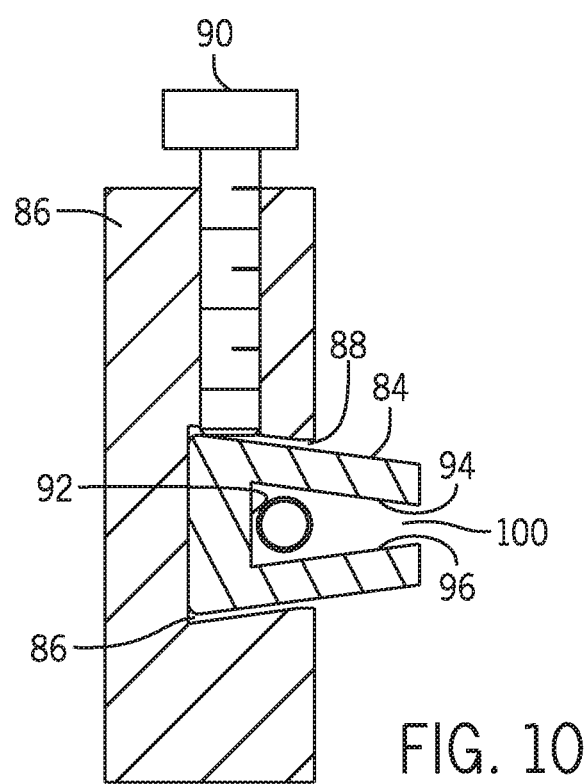
FIG. 10 is a cross sectional view of the track.

Referring to FIG. 3 and FIG. 10 a track 86 includes a channel 88. A set screw 90 or other type of fastener extends through track 86 into channel 88 to secure sleeve 84. In one embodiment sleeve 84 includes a first wall 92 and a second wall 94 and a third wall 96 extending from first wall 92 forming a cavity 98. An opening 100 is defined as the space between the two free ends of second wall 94 and third wall 96. In another embodiment, sleeve 84 may be formed by a single arcuate wall member having an opening 100. A disposable sterile barrier sleeve such as a plastic sleeve may be located about track 86 such that when sleeve 84 is isolated from track 86. Sleeve 84 may be a single use device and disposed of once a medical procedure using the sleeve is complete. In another embodiment, no sleeve 84 is placed into channel 88, rather a sterile barrier may be placed within channel 88 to isolate a guide catheter from the walls of channel 88. In an alternative embodiment, no sleeve or sterile barrier is employed and track 86 is a single use device that is discarded after use and replaced prior to the use of the bedside system with another patient or for another procedure.

Referring to FIG. 7 and FIG. 8 track 86 includes a distal end 102 that is configured to be located proximate a patient, and an opposing proximal end 104. A track longitudinal axis 106 is defined by the longitudinal axis of the track 86 extending between proximal end 104 and distal end 102. In one embodiment track longitudinal axis 106 and hemostasis valve longitudinal axis 50 form an acute angle 108. In one embodiment angle 108 is preferably between 25 and 45 degrees, and more preferably between 30 and 45 degrees. In one embodiment angle 108 is 30 degrees.

In one embodiment plane track longitudinal axis 106 forms an acute angle 112 with a horizontal plane defined by gravity that also represents the horizontal plane of a bed or procedural surface that a patient lies on. Track longitudinal axis 106 and hemostasis valve first leg longitudinal axis 50 form a plane 110. In one embodiment plane 110 is at an acute angle 108 with respect to the horizontal plane. In other embodiments, the angle formed between plane 110 and the horizontal may be an acute angle different than the angle formed by track longitudinal axis 106 and the horizontal plane.

Referring to FIGS. 7 and 8 guide catheter mechanism 26 is offset to one side of track 86, as a result plane 110 is not perpendicular to the horizontal plane. In one embodiment guide catheter mechanism 26 is located closer to an operator than track 86. Stated another way, when an operator operates guide catheter mechanism 26 the operator will be closer to the guide catheter mechanism than the track.

Referring to FIG. 3, in one embodiment, track 86, guide catheter mechanism 26 and cassette 118 may be rotated downwardly about axis y such that guide catheter mechanism 26 and cassette 118 are easier to access by an operator facing guide catheter mechanism 26 and cassette 118. In one embodiment, the vector shown as x is perpendicular to the longitudinal axis 106 extends through channel 88 and forms an angle 166 below a horizontal plane. In one embodiment angle 166 is 15 degrees below a horizontal plane as defined by gravity. In one embodiment an operator is located proximate a first side a patient's bed. A support is located on one side of the bed typically opposite the first side. The cassette 118 and guide catheter mechanism 26 is closer to the first side of the patient's bed than track 86. In this way, the operator or physician has easy access to the cassette 118 and guide catheter mechanism 26. By tilting the cassette 118 and guide catheter mechanism downwardly toward the patient's bed such that the portion of the cassette 118 and guide catheter mechanism 26 closer to track 86 is higher vertically than the portion of the cassette 118 and guide catheter mechanism 26 that is furthest from track 86. Additionally, by pivoting guide catheter mechanism 26 and cassette 118 from the longitudinal axis 106 by angle 108, the guide catheter mechanism and cassette 118 is located in a position that allows for access by the operator and/or physician.

Track 86 is secured to a bedside support 114 and is maintained in a fixed position relative to patient bed 22. Bedside support 114 may be secured directly to a side of patient bed 22 or may be secured to a floor mounted support that is either fixed relative patient bed 22 or positioned on a floor proximate patient bed 22 such that track 86 is in a fixed location with respect to patient bed 22 or to a patient on patient bed 22 during a catheter based procedure. In one embodiment, the orientation of track 86 may be adjusted with respect to patient bed 22 so that angle 112 may be adjusted as well. In another embodiment angle 112 may be between ten degrees and forty five degrees and in one embodiment angle 112 may be thirty degrees.

Figure 12:
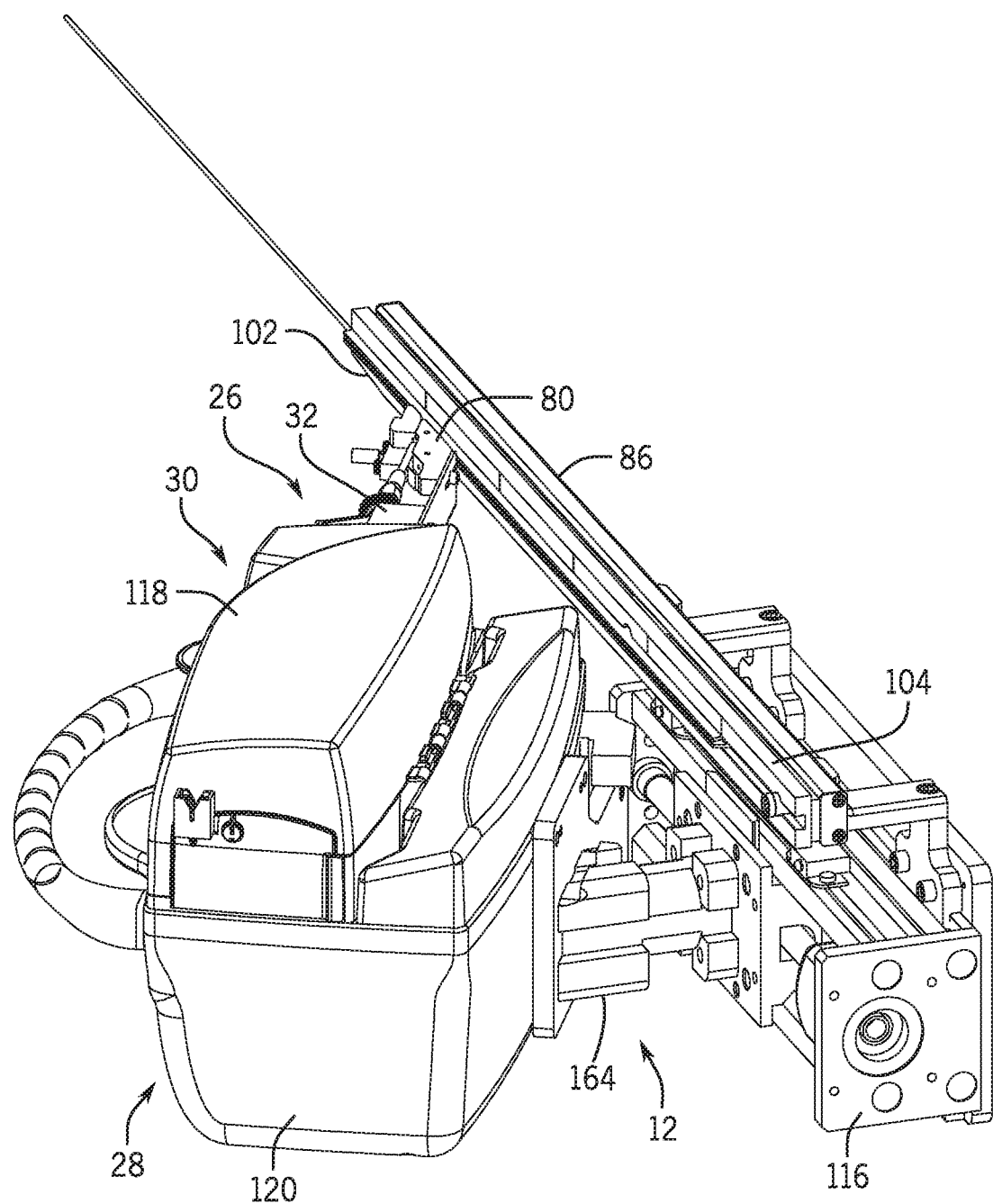
FIG. 12 is a rear isometric view of the catheter bedside system.

Referring to FIG. 12 guide catheter mechanism 26 may be secured to a linear actuator 116 to translate guide catheter mechanism along an axis parallel to or co-linear with track axis 106. The linear actuator 116 may provide for discrete incremental movement or may provide for continuous movement. In one embodiment the linear actuator includes a rack and pinion and in another embodiment includes a robotic arm. Linear actuator 116 moves independently of track 86. As discussed above working catheter mechanism 28 and guide wire mechanism 30 may be included in a cassette 118 that is operatively removably secured to a base member 120. Base member 120 and guide catheter mechanism 26 may be operatively secured to linear actuator 116 with a support 164, such that guide catheter mechanism 26, working catheter mechanism 28, and guide wire mechanism 30 are translated together along a linear axis.

The operation of the guide catheter mechanism 26 during a catheter procedure will now be described using an exemplary embodiment. A patient in need of a catheter based procedure will lie in a supine position on patient bed 22. An opening in the femoral artery will be prepared for the introduction of a guide catheter 122.

Track 86 will be positioned relative to the patient such that distal end 102 of track 86 is located proximate the femoral artery of the patient. Track 86 is covered with a sterile barrier and a single used sleeve 84 is positioned in channel 88. Typically track 86 will be covered with a sterile barrier prior to positioning relative to the patient. As sleeve 84 is positioned in channel 88 the sterile barrier is placed into channel 88 such that the sterile barrier provides a guard against any fluids that may be exposed on sleeve 84 from contacting track 86. Sleeve 84 has a distal end 124 and a proximal end 126. Distal end 124 of sleeve 84 is located proximal distal end 102 of track 86. In one embodiment, sleeve 84 may have certain geometry to provide for placement within channel 88 of track 86 and to facilitate entry and removal of a portion of guide catheter 122.

In one catheter procedure on the heart of a patient, a guide catheter 122 of appropriate length is selected based on the size of the patient. Guide catheter 122 has a proximal end 128 and a distal end 130. In one embodiment, proximal end 128 is first connected to rotating luer connector 48 of hemostasis valve 34. Distal end 130 is then manually inserted into the femoral artery of the patient and positioned such that distal end 130 of the guide catheter 122 is located adjacent the ostium of the heart. It is also contemplated that proximal end 128 of guide catheter 122 may be connected to rotating luer connector 48 after distal end 130 is positioned adjacent the ostium.

Once guide catheter 122 is properly positioned relative to the patient's heart, a central portion 132 of guide catheter 122 located outside of the patient is placed within sleeve 84 by pushing a central portion 132 of guide catheter 122 through opening 100 into cavity 98.

Figure 9:
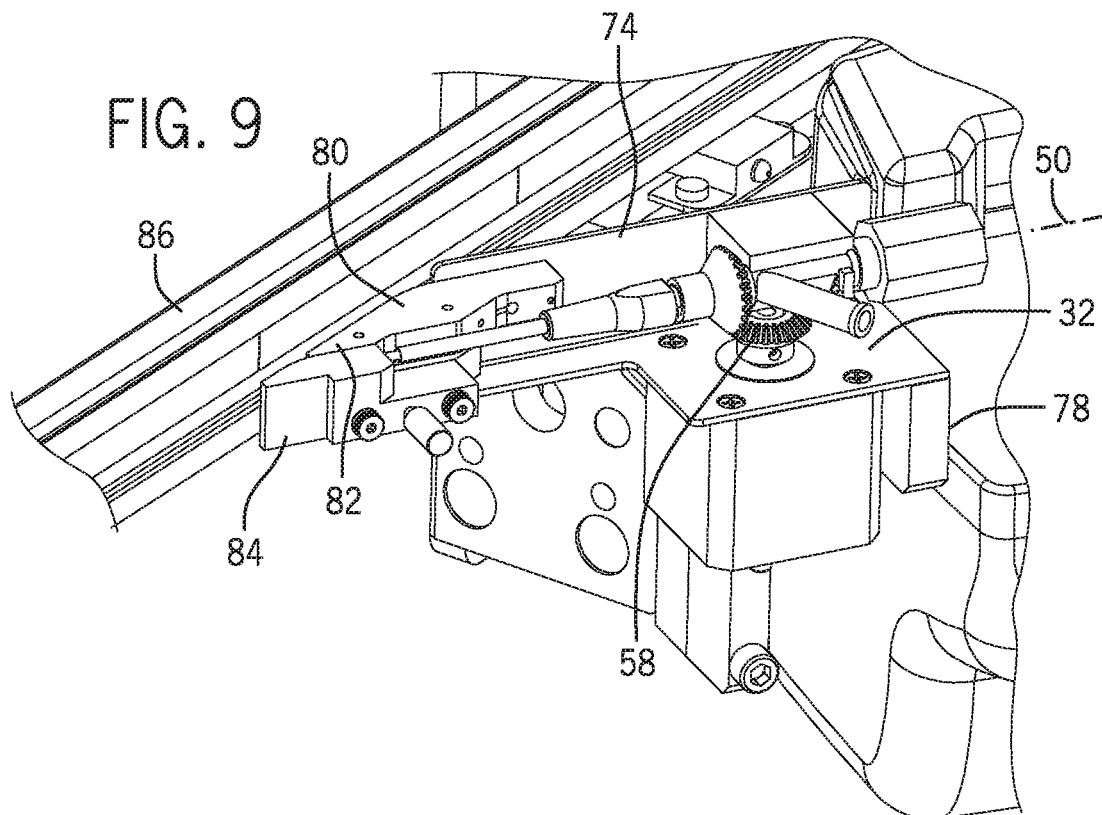
FIG. 9 is an isometric view of the guide catheter drive mechanism and track.
Figure 11:
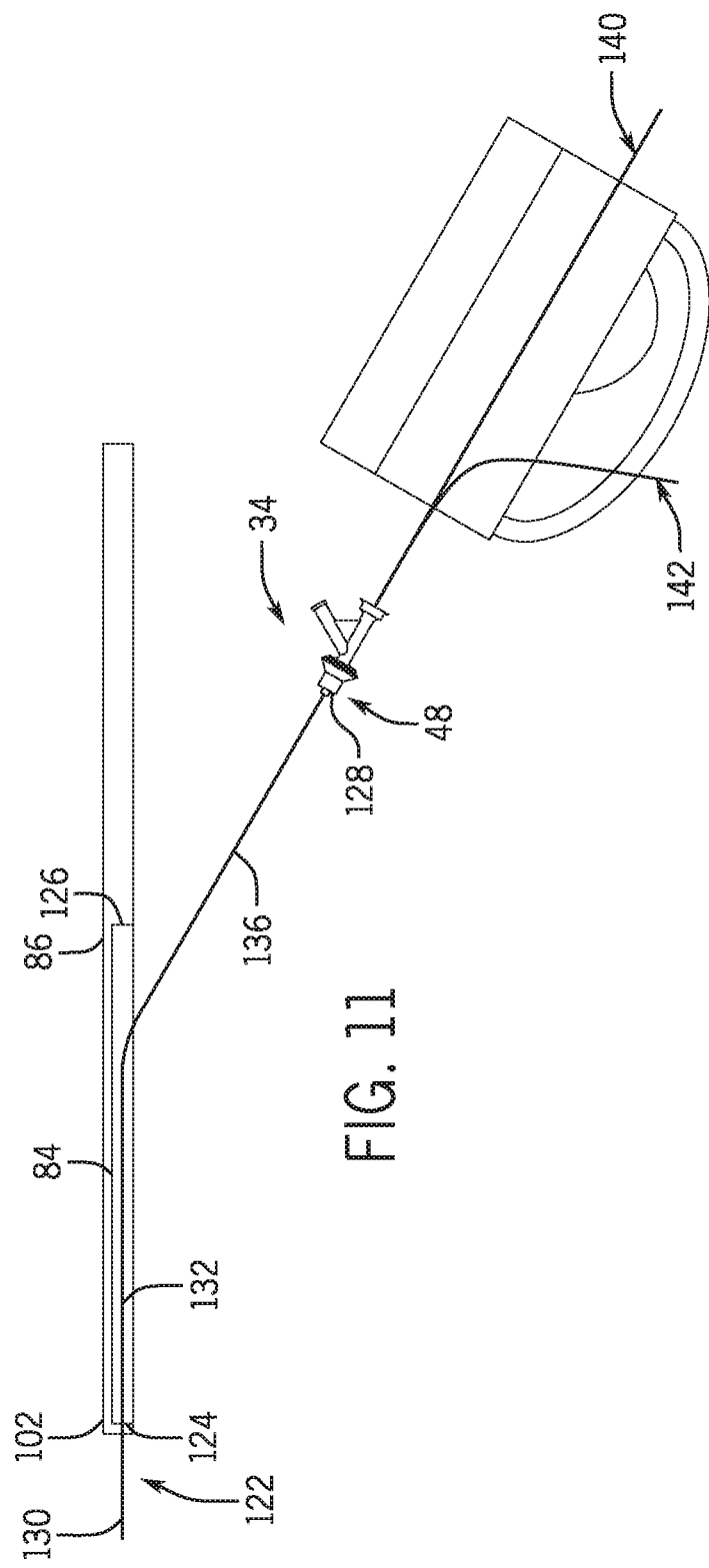
FIG. 11 is a top schematic view of the hemostasis valve, guide wire, working catheter, and guide catheter.

Referring to FIG. 9 and FIG. 11, an entering portion 134 of guide catheter 122 will be exposed between distal end 102 of track 86 and the patient. Additionally, a connecting portion 136 adjacent proximal end 124 of guide catheter 122 extends outwardly from sleeve 84 and track 86 in a direction toward guide catheter mechanism 26. In one embodiment, connecting portion 136 has sufficient length to allow for the guide catheter hub to be connected to rotating luer 52 and have sufficient length to bend into track 86. Connecting portion 136 extends outwardly from sleeve 84 at angle between approximately 25 to 45 degrees and 30 in but may be between 30 and 45 degrees and may be 30 degrees. Guide portion 82 guides guide catheter from support 80 into track 86. Guide portion 82 may include a curved surface to assist in the transition of the guide catheter into track 86.

Proximal end 128 guide catheter 122 is connected to rotating luer connector 48. In one embodiment, proximal end 128 of guide catheter 122 is connected to rotating luer connector 48 of hemostasis valve 34 prior to distal end 124 of catheter 122 being inserted into the patient or prior to central portion 132 being positioned within sleeve 84. Hemostasis valve 34 is secured to base 32 with a quick release mechanism 138 such that driven gear 56 is engaged with drive gear 58. Driven gear 56 located on external surface 52 of rotating luer connector 48 is moved in a direction toward drive gear 58 to engage driven gear 56 with drive gear 58. Quick release 138 is then closed to releasably capture hemostasis valve 34. In an engaged position proximal end 46 of second leg 44 of hemostasis valve extends away from track 86 and having a horizontal vector component. Stated another way in a preferred embodiment, second leg working plane defined by axis 50 of first leg 38 and axis 70 of second leg 44 does not define a plane that is perpendicular to a horizontal plane defined by gravity or by a horizontal plane defined generally by the top surface of the patient's bed 22.

Guide Catheter mechanism 26 is moved linearly by linear actuator 116 to allow proper alignment of proximal end 126 of guide catheter 122 with guide catheter mechanism 26. Guide catheters are typically sold with varying lengths and selected depending on the size of the patient. However, since the length of the guide catheter required varies from patient to patient, it may be necessary to adjust the position of the hemostasis valve quick release for each patient. In one embodiment hemostasis valve quick release may be adjusted along an axis parallel to track axis 106 relative to base 32. In another embodiment, base 32 may be moved along an axis parallel to track axis 106 to properly position hemostasis valve 34 so that guide catheter 122 is properly positioned relative to the patient.

Linear adjustment of hemostasis valve along an axis parallel to track axis 106 may be done manually or may be controlled by user interface 18 at work station 14 that is typically remote from bedside system 12. Work station 14 communicates with bedside system through a wireless or wired connection. In this embodiment, an operator manipulates user interface 18 such as a joy stick or touch screen to provide a control signal to a linear actuator motor to move base 32 relative to track 86.

Once guide catheter 32 is secured to hemostasis valve 34 and hemostasis valve 34 is secured to base 34 with quick release 138 a guide wire 140 and/or working catheter 142 is introduced into the proximal end 42 of first leg 38. Proximal end 42 of first leg 38 includes a valve member 162 such as a Tuohy Borst adapter. Tuohy Borst adapters are known in the art and operate to adjust the size of the opening in proximal end 42 of first leg 38 of hemostasis valve 34 to minimize the risk that fluids may exit the proximal end 42 of first leg 38. Other types of adapters known in the art may also be used with hemostasis valve 34 to adjust the size of the opening in proximal end 42 of first let 38.

During a catheter procedure it may be necessary to reseat distal end 124 of guide catheter 122 within the ostium of the patient. An operator may rotate guide catheter 122 by providing a control signal to motor 60 to rotate drive gear 58 in a clockwise or counterclockwise direction. As a result driven gear 56 rotates causing rotation of rotating luer connector 48 and rotation of guide catheter 122. In addition to a requirement to rotate guide catheter 122 it may also be necessary during a catheter procedure to move guide catheter 122 along track axis 106 to properly position distal end 124 of guide catheter 122. Work station may also include a user interface such as a joy stick, button, touch screen or other user interface to control a linear actuator to move guide catheter mechanism 26 in a direction substantially parallel to track axis 106. Movement in a first direction in parallel to track axis will result in movement of guide catheter 122 further into the patient and movement of the linear translator in an opposing second direction will result in movement of guide catheter 122 outwardly from the patient.

If an operator wishes to remove guide catheter 122, working catheter 142 and/or guide wire 140 during a catheter procedure, the operator releases quick release 138 and removes hemostasis valve 34 along with guide catheter 122 and working catheter 142 and/or guide wire 140. Central portion 132 of guide catheter 122

Working catheter 142 and guide wire 140 may be removed from their respective working catheter mechanism 28 and guide wire mechanism 30 as described in U.S. Pat. No. 7,887,549. Once guide catheter 122, 140 hemostasis valve 34, working catheter 142 and guide wire 140 are removed from guide catheter mechanism 26, working catheter mechanism 28 and guide wire mechanism 30 an operator may manipulate guide catheter 122, working catheter 142 and guide wire 140 manually.

Figure 13:
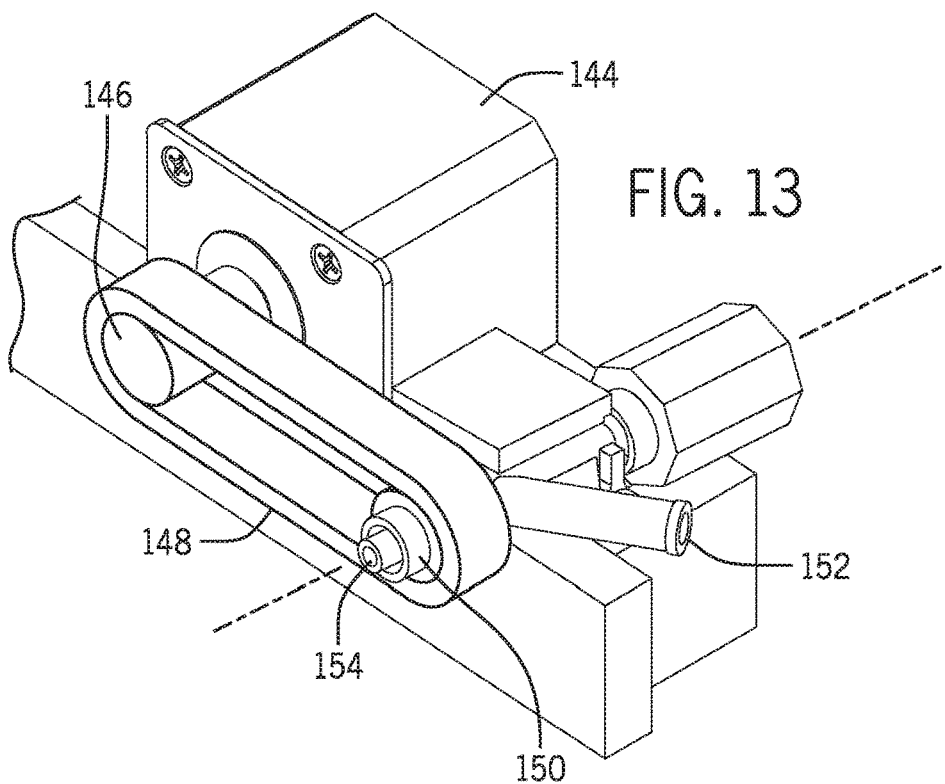
FIG. 13 is an alternative hemostasis valve and guide catheter drive mechanism.

Referring to FIG. 13 an alternative embodiment of a drive for rotational luer connector includes a motor 144 rotating a first pulley 146 driving a belt 148 such as a timing belt. Belt 148 is connected to the outer surface 150 of a pulley 152 about the outer surface 150 of a rotational luer connector 156. First pulley 146 may include a plurality of teeth that mesh with ribs on belt 148 and the outer surface 150 of rotational luer connector 154 also include a plurality of teeth that mesh with ribs on belt 148. In this manner control of motor 144 allows for controlled rotation in a clockwise and counterclockwise of rotational luer connector 156 thereby rotating guide catheter 122 attached thereto. In one embodiment pulley 152 and bevel gear 56 are integrally formed with the outer surface of rotating luer connector. However, it is also contemplated that a collet having an outer surface defining a pulley or bevel gear may be secured to the outer surface of rotating luer connector.

Figure 14:
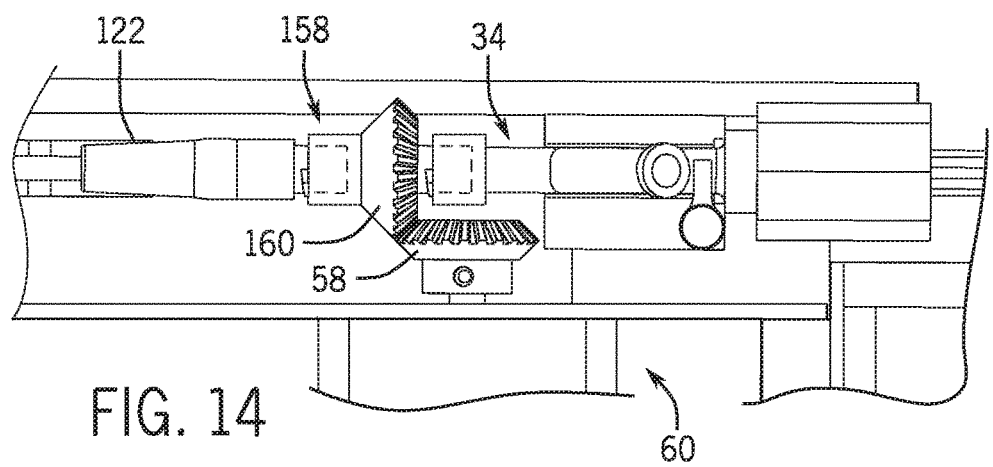
FIG. 14 is a partial side view of the hemostasis valve and guide catheter.

Referring to FIG. 14, in another embodiment, a luer extension member 158 may act to connect proximal end 128 of guide catheter 122 to rotating luer connector 48. Luer extension member 158 may include an outer surface having a gear 160 or pulley member to be operatively connected to the rotational drive motor 60 via drive gear 58. In this embodiment, the rotational drive motor is operatively coupled to the outer surface of luer extension member and not directly to the outer surface of the rotating luer connector. This permits the use of presently available commercially available hemostasis valves. Additionally in a further embodiment a luer extension member may include a rotating portion such that the distal end of the hemostasis valve need not have a rotational luer connector but rather include a non-rotational luer connector. Extension 158 includes a female luer connector on the distal end to removably receive a male luer fitting on a guide catheter. Extension 158 also includes a male luer connector on the proximal end that is removably received within a female luer connector of a rotating connector on a Hemostasis valve. Note that in one embodiment, gear 160 is a beveled gear with teeth facing the proximal end.

Figure 15:
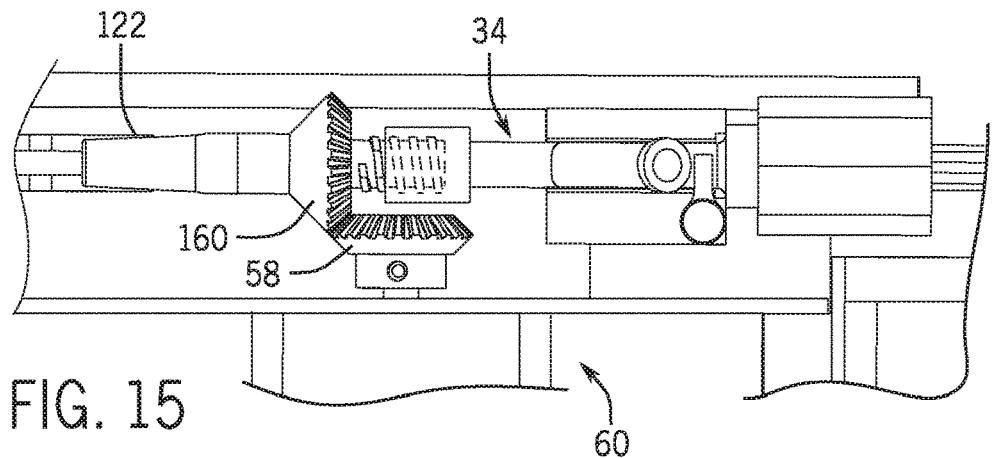
FIG. 15 is a partial side view of an alternative guide catheter hub and guide catheter drive mechanism.
Figure 16:
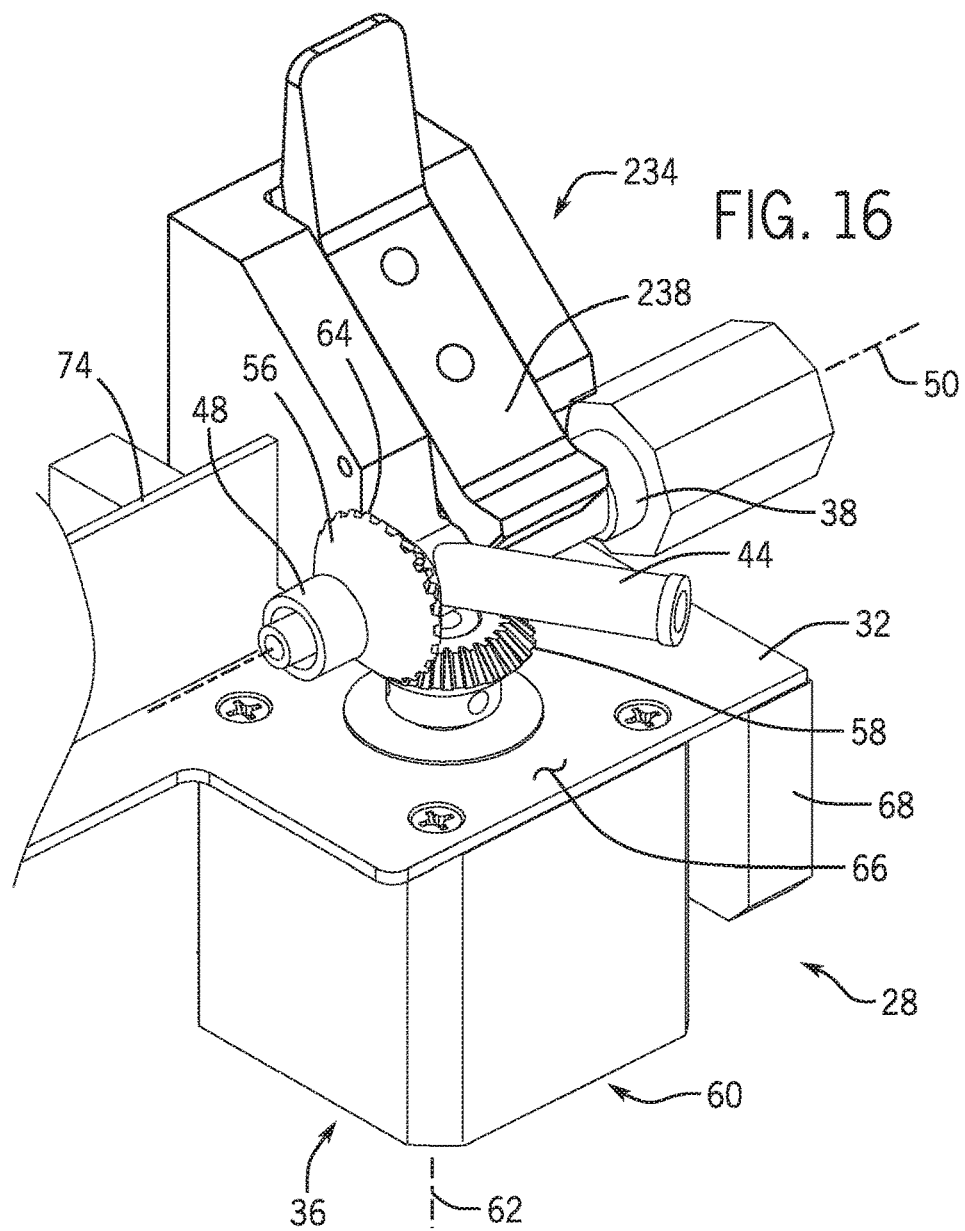
FIG. 16 is an isometric view of a quick release for a hemostasis valve.
Figure 17:
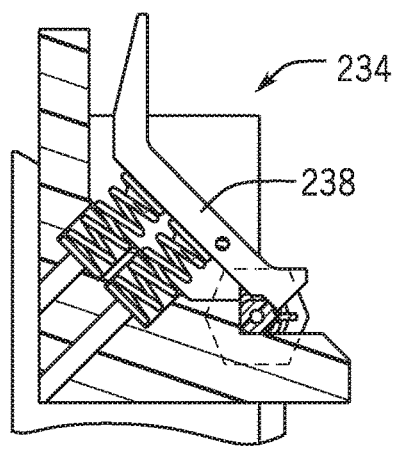
FIG. 17 is a cross sectional view of a portion of the quick release of FIG. 16. in an engaged position.
Figure 18:
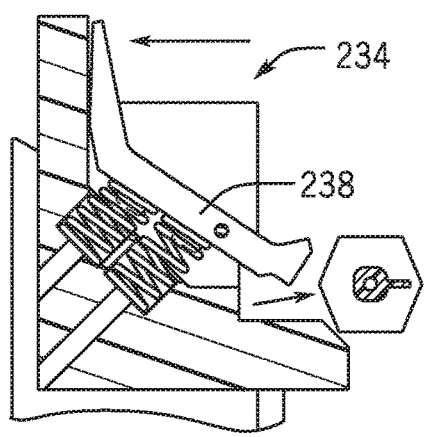
FIG. 18 is a cross sectional view of a portion of the quick release of FIG. 16. in a disengaged position.

Referring to FIG. 15 in another embodiment, a hub of guide catheter 122 may have gear formed therewith or attached thereto to connect to a rotating luer of hemostasis valve 34.

Figure 19:
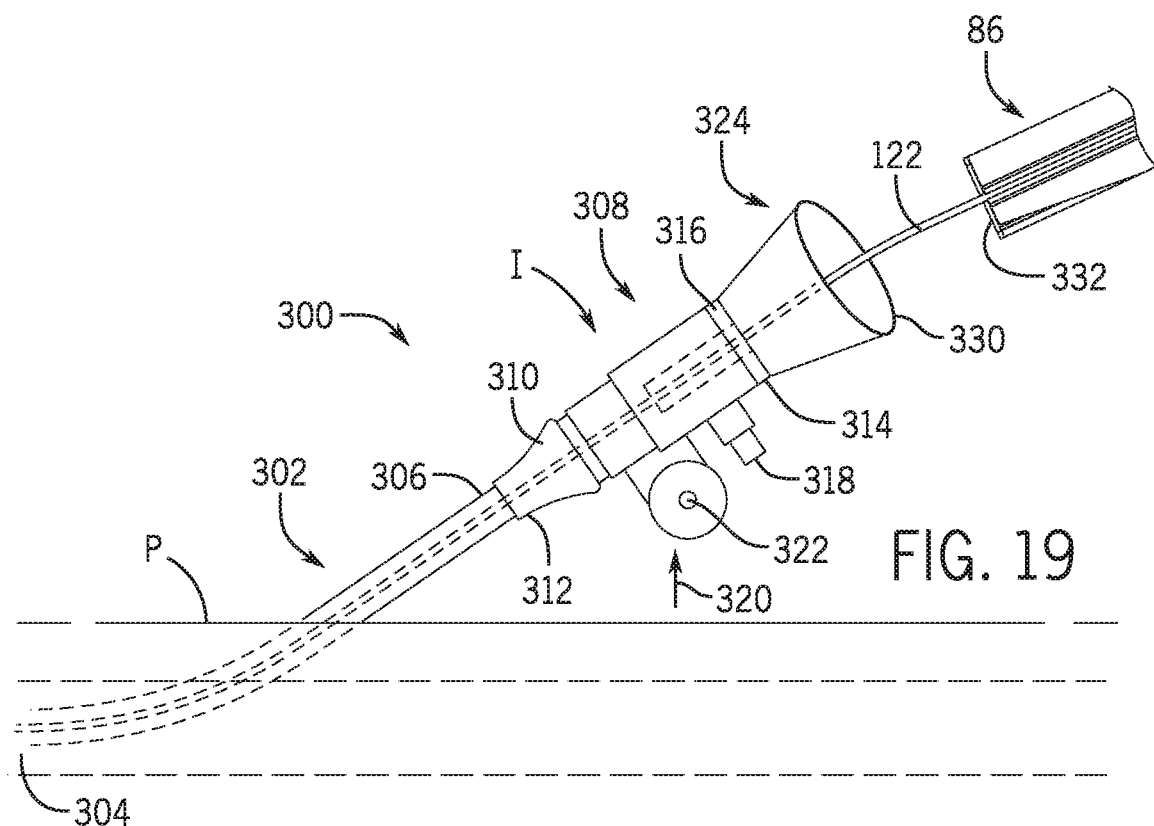
FIG. 19 is a side isometric view of an introducer connector.

Referring to FIG. 19 an introducer 300 includes a sheath 302 having a distal end 304 and a proximal end 306. Sheath 302 is a tubular shaft that is coupled in fluid communication with a coupler 308 at proximal end 306 of sheath 302. Coupler 308 includes a distal end 312 having a funnel or frusto conical shape member 310 providing a transition between coupler 308 and the proximal end 306 of sheath 302. Coupler 308 includes a proximal end 314 provide with a hemostasis valve 316 to provide a fluid tight seal for a guide catheter, working catheter such as a balloon and stent, and/or a guide wire. Coupler 308 also includes a side port 318 that is in fluid communication with sheath 302 through an interior of coupler 308. Side port 318 allows for introducing a flushing solution such as a saline solution, or a contrast agent or medication into the vein through sheath 302. Side port 318 may also be used to withdraw material such as blood from the patient's vein. Coupler 308 also includes a disk engagement member 320 that includes an opening 322 through which a suture may secure coupler 308 to a patient's skin to stabilize coupler 308 relative to the patient. Disk engagement member 320 may also provide a connector to a support that is located on or adjacent to a patient to stabilize coupler 308.

Figure 20:
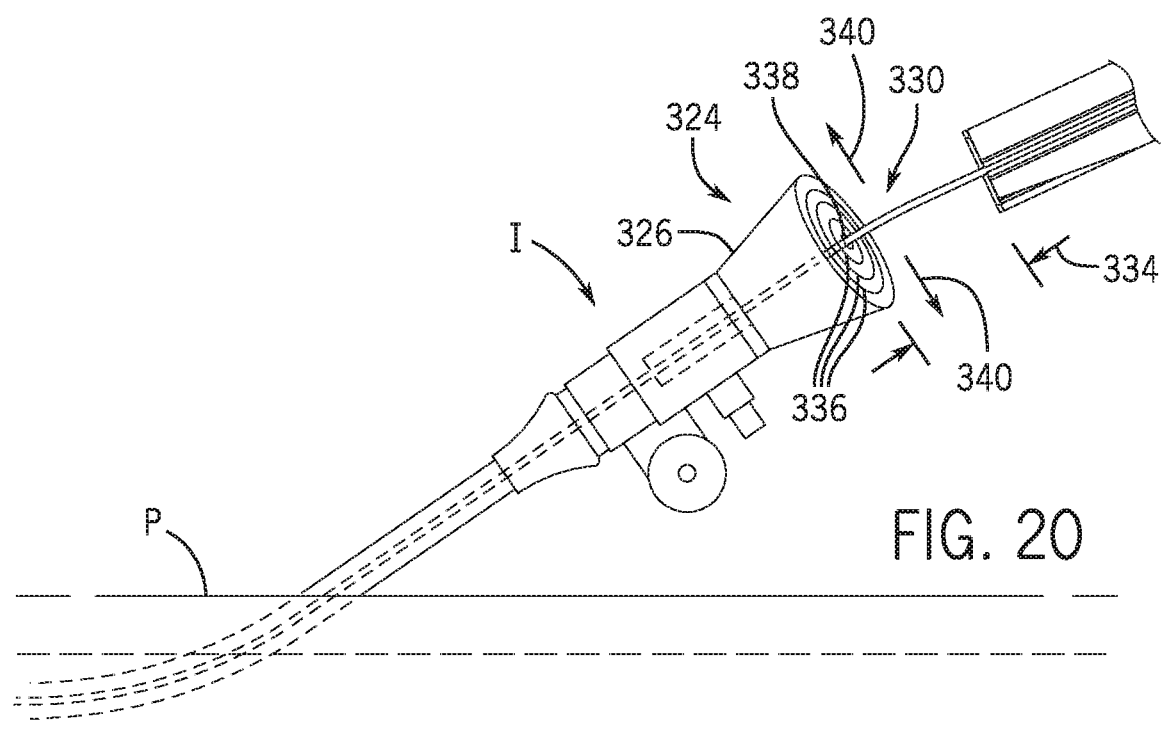
FIG. 20 is a side isometric view of the introducer connector of FIG. 19 with a movable opening.

Referring to FIG. 19 and FIG. 20 an introducer connector 324 is releasably secured to proximal end 314 of coupler 308. In one embodiment, introducer connector 324 includes a distal end 326 is releasably secured to proximal end 314 adjacent to hemostasis valve 316 in such a manner that hemostasis valve 316 is not blocked. Introducer connector 324 includes a body 328 that is funnel shaped or frusto conically shaped and configured to guide a guide catheter, working catheter or guide wire into coupler 308. Body 328 includes a proximal opening 330 through which guide catheter 122 extends.

Guide catheter 122 that extends from track 86 or sleeve 84 will enter opening 330 and exit through a bottom opening that is adjacent hemostasis valve 316. In one embodiment proximal opening 330 of body 328 is located proximate to a distal end 332 of track 86 such that there is a distance 334 between distal end 332 of track 86 and opening 330. As patient P moves relative to track 86 the distance 334 will change. If distance 334 is too great guide catheter 122 may begin to buckle prior to entering coupler 308. The term buckle or buckling as used herein means that guide catheter begins to take a non-linear shape without a portion bending over on itself that would prohibit fluid and/or a working catheter from being extended through the guide catheter. The term kink or kinking as used herein means that a portion of the guide catheter is bent over on itself sufficiently such that the shape of the guide catheter inhibits movement of a working catheter within the guide catheter.

When a patient moves relative to the distal end 332 of track 86 guide catheter may begin to buckle. The inner surface of introducer connector 324 acts to direct guide catheter toward introducer coupler 308 without kinking as guide catheter enters opening 314. In one embodiment, opening 330 of introducer connector 324 extends beyond a terminal end 332 of track 86 in a direction away from introducer 308. In this embodiment, although introducer connector 324 is not connected to track 86, there is no portion of guide catheter 122 that is exposed between track 86 and coupler 308. In this configuration, distal end 332 track 86 may move in a fore aft direction away from hemostasis valve 316 while remaining within the interior of introducer connector 324.

Referring to FIG. 20 introducer coupler 308 includes a movable top portion 334 proximate opening 310. Movable top portion 334 includes a number of overlapping floating disks 336 that allow the disks to move from side to side as illustrated with arrows 340. Though floating disks may be movable in any vector direction in a plane defined by the opening 330. Top portion 334 allows guide catheter 122 to extend through a central opening 338 while keeping the interior of introducer connector 324 covered.

Figure 21:
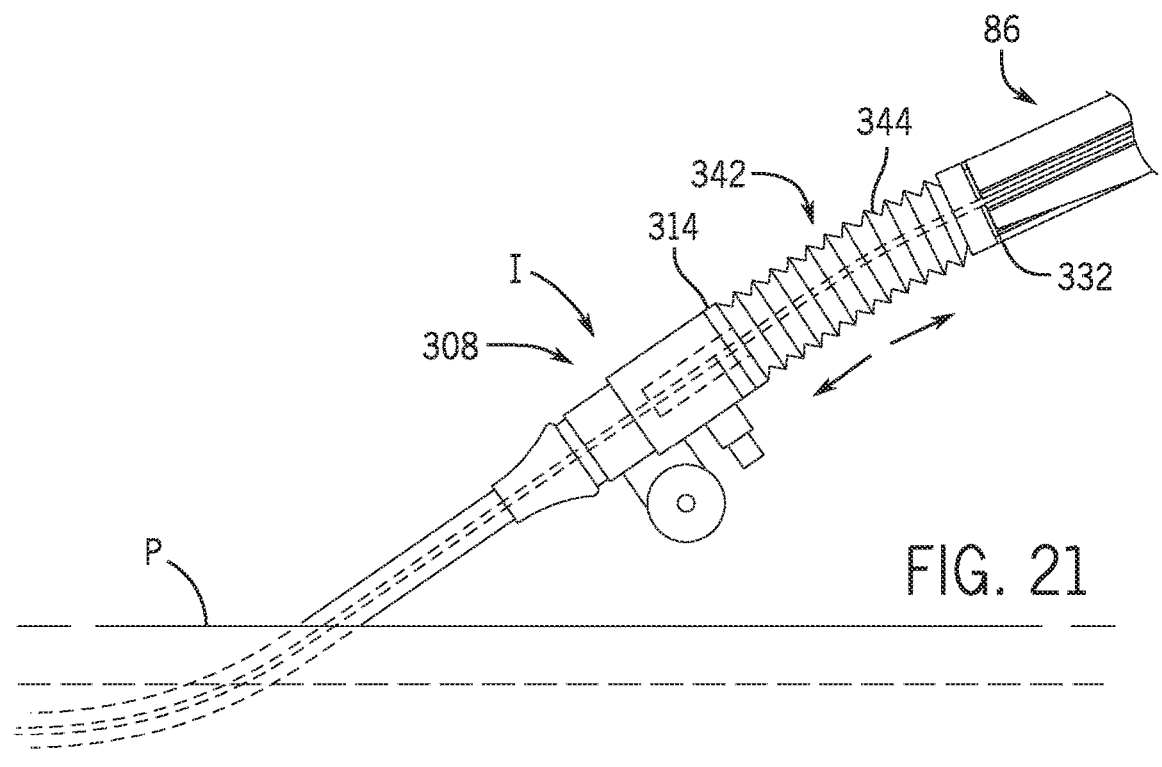
FIG. 21 is a side isometric view of a second embodiment of an introducer connector.

Referring to FIG. 21 a connector 342 is operatively secured to proximal end 314 of coupler 308 and a distal end 332 of track 86. Connector 342 includes an accordion style body 344 that allows the connector 342 to become longer and shorter as the patient moves relative to track 86. In this way the accordion folds collapse or expand to permit connector 342 to have a greater or lesser distance.

Figure 22:
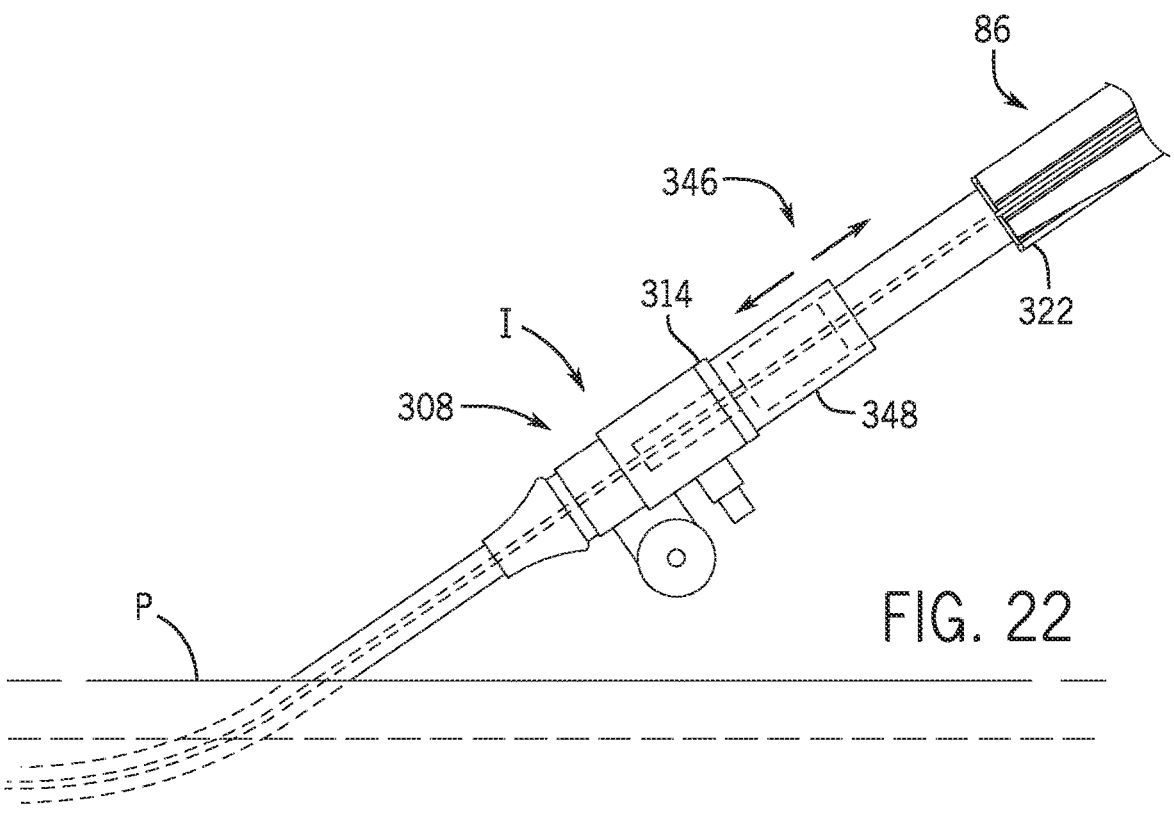
FIG. 22 is a side isometric view of a third embodiment of an introducer connector.

Referring to FIG. 22 in another embodiment, a connector 346 includes telescoping members 348 with one of the telescoping members operatively secured to proximal end 314 of coupler 308 and another of the telescoping members operatively secured to distal end 332 of track 86. The telescoping members moving relative to one another to allow the distance between the patient and the track to vary, while still maintaining a continuous connection between the coupler 308 ad track 86. The continuous connection provides a path for guide catheter 122 that avoids buckling and/or kinking. Telescoping connector may include two or more telescoping members.

Figure 23A:
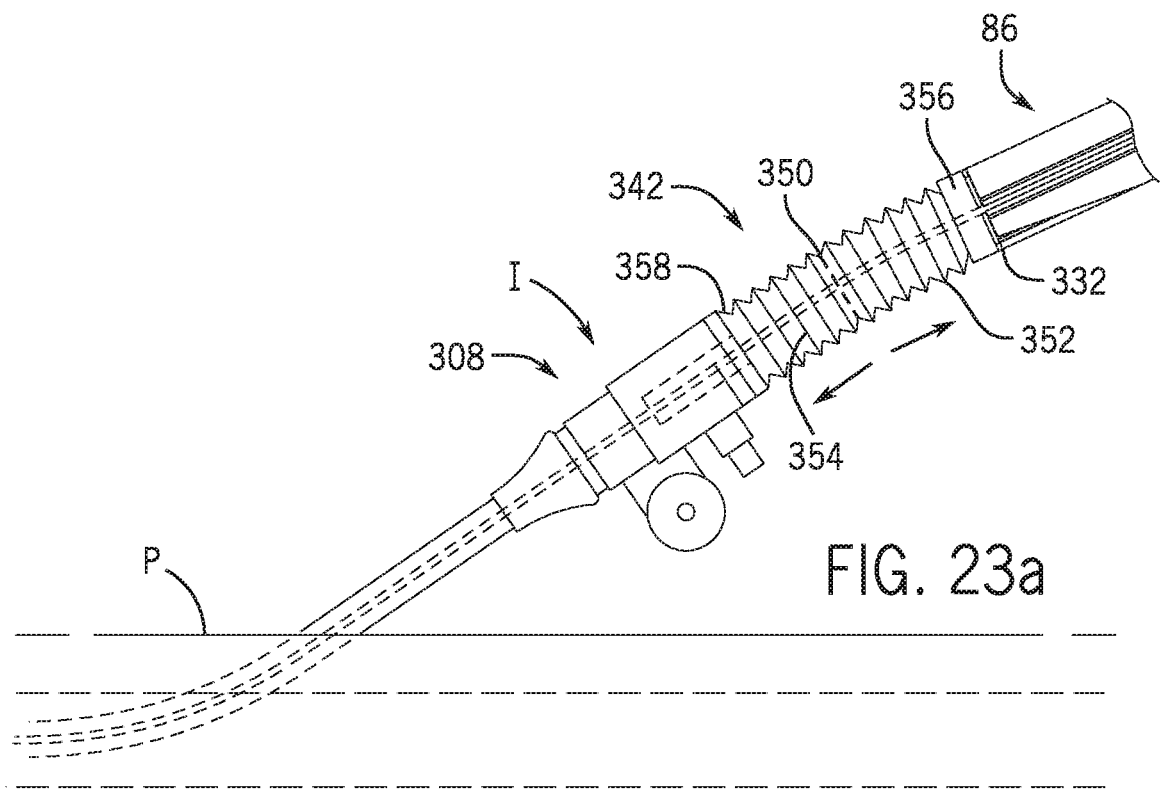
FIG. 23a is a side isometric view of the introducer of FIG. 21 with a breakaway portion.
Figure 23B:
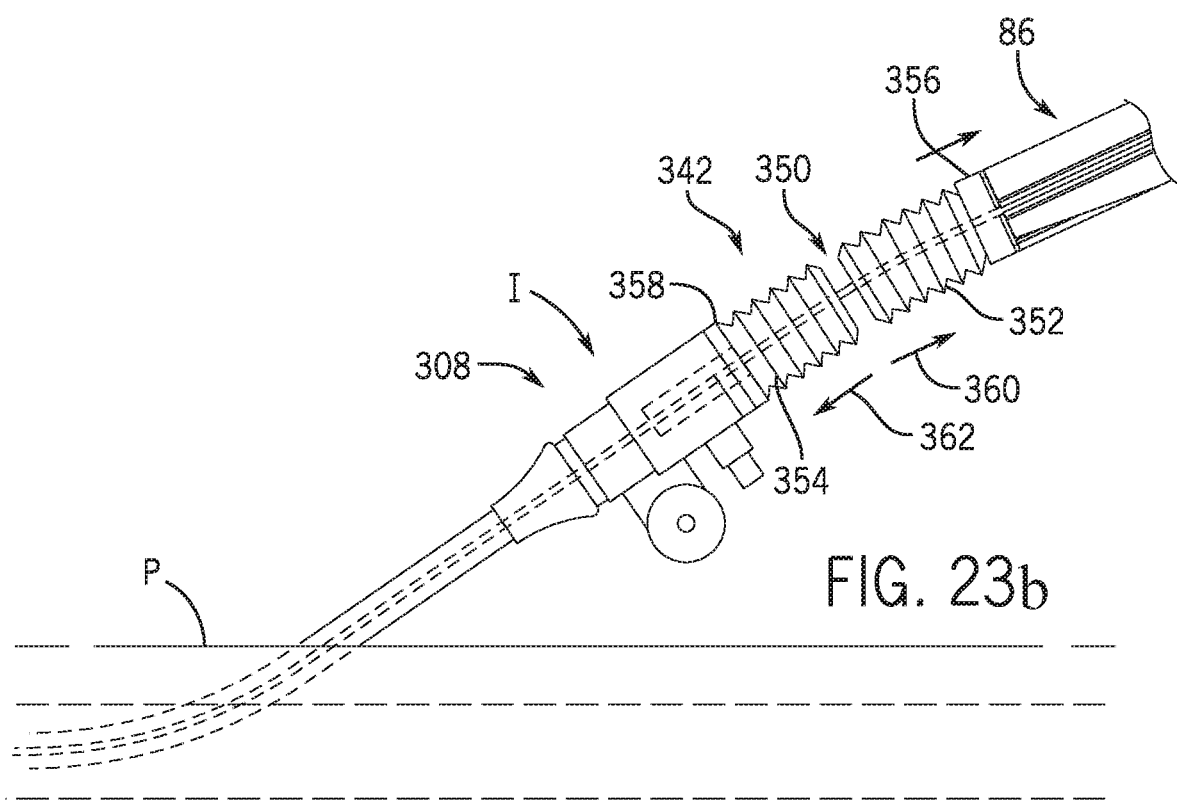
FIG. 23b is a side isometric view of the introducer connector of FIG. 21 with a breakaway portion in the separated position.
Figure 24:
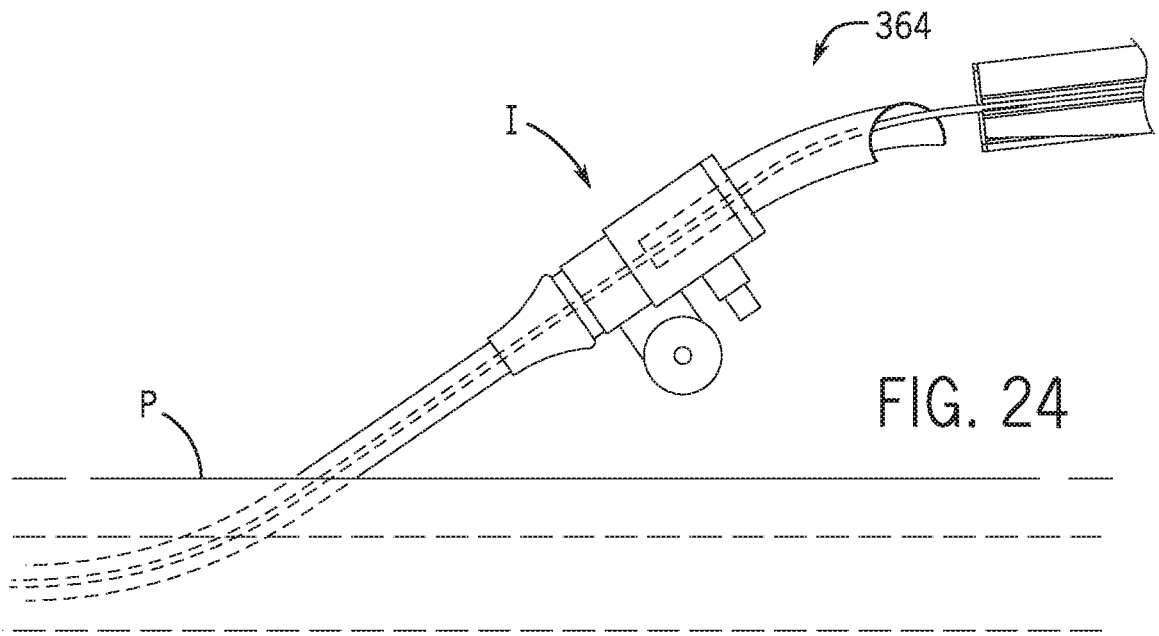
FIG. 24 is a side isometric view of another introducer connector.

Referring to FIG. 23 and FIG. 24 another embodiment of accordion connector 342 includes a breakaway portion 350 that separates a first portion 352 of accordion connector 342 from a second portion 354 of accordion connector. If accordion connector 342 is stretched too far instead of exerting a force on introducer 300 that could result in introducer being pulled away from the patient. Breakaway portion 350, may be formed from a frangible region that is designed to fracture upon a predetermined force. Alternatively, a medically safe adhesive may be used that would permit separation of the first portion 352 from the second portion 354 upon the exertion of a predetermined force. In another embodiment, a hook and loop connector such as Velcro may be used to provide a breakaway connection at the interface between the first portion 352 and second portion 354 forming breakaway portion 350. In a further embodiment, magnetic members may be located at the interface between first portion 352 and second portion 354 to provide a connection between first portion 352 and second portion 354 until a predetermined force is applied to the connector as represented by vector directions 360, 362.

FIG. 23a illustrates a connector 342 with the breakaway portion 350 still in a connected or in a non-separated position. FIG. 23b illustrates a connector 342 with the breakaway portion 350 in the separated position.

While breakaway portion 350 may be located in a center location between a proximal end 356 and a distal end 358. However breakaway portion 350 may be located adjacent one or both of proximal end 356 and distal end 358. In an alternative embodiment, one of the proximal end 356 and distal end 358 may have a breakaway connection with distal end 332 of track 86 or proximal end 314 of coupler 308. In another embodiment, the breakaway connection between connector 342 and the track and/or the coupler 308 may be friction connection such that once a predetermined force is applied to the friction connection, connector 342 will separate from track 86 and/or coupler 308. While the examples provided for a breakaway connection was described with connector 342, a breakaway feature may be added to other connection members operatively connecting coupler 308 or an introducer sheath 300 with a track 86 or any other portion of a robotically controlled catheter system.

In another embodiment, connector 342 may have sufficient flexibility that upon a predetermined compressive force applied to the distal end and proximal end of connector 342, connector 342 buckles ensuring that there the pressure applied to the introducer sheath 300 does not exceed a predetermined force when the track is moved toward the coupler 308 and/or the patient.

Referring to FIG. 24 in another embodiment a connector 364 includes a housing forming an inverted U shape channel to guide the guide catheter 122 into coupler 308. Other shapes are also contemplated such as a C shaped channel. Connector 364 may be secured to distal end 332 of track 86 or may be secured to proximal end 314 of coupler 308, or may be secured to both track 86 and coupler 308. Connector 364 may also have a breakaway connection and/or sufficient flexibility to bend if track 86 is moved toward coupler 308.

Figure 25:
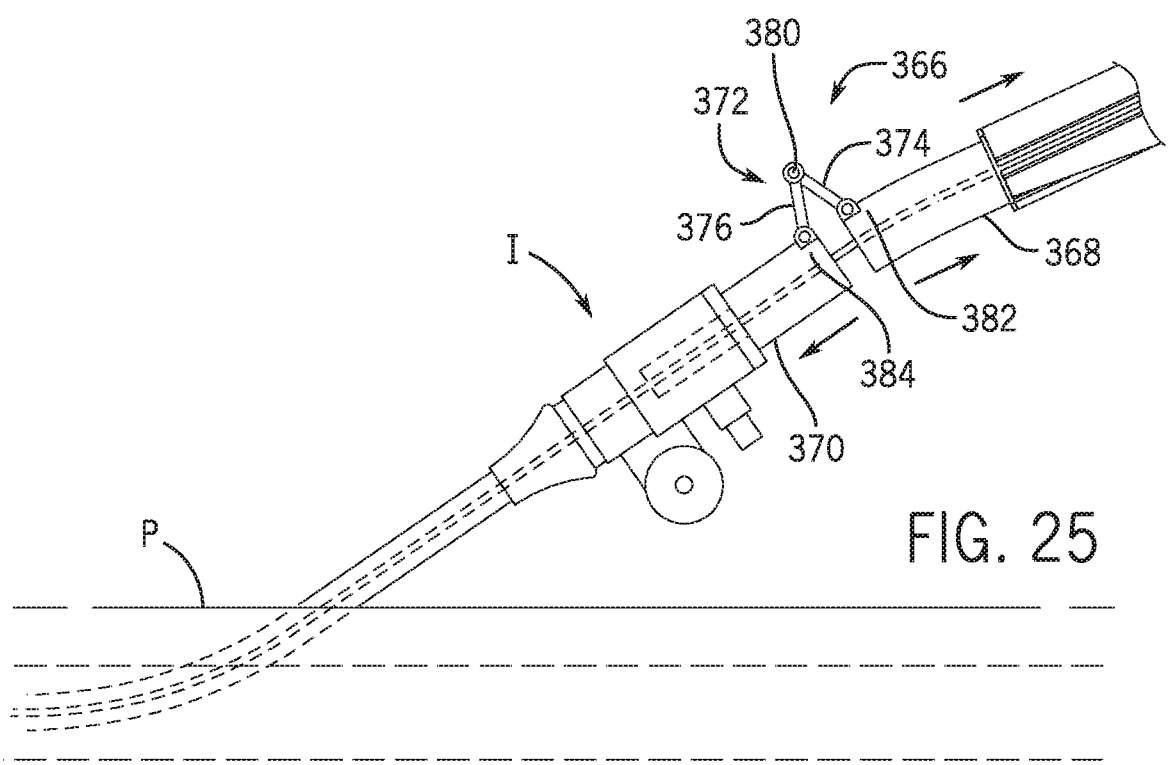
FIG. 25 is a side view of another embodiment of an introducer connector.

Referring to FIG. 25 in a further embodiment a connector 366 includes a first portion 368 and a second portion 370 operatively coupled together with an expanding member 372. In a neutral position, first portion 368 and second portion 370 are separated by a distance that provides sufficient guidance to guide catheter such that it will not buckle or bend. Expanding member 372 has a first leg 374 coupled to first potion 368 and a second leg 376 coupled to second portion 370. Expanding member allows first portion 368 and second portion 370 to move toward and away from one another as track 86 moves toward and away from the patient. Expanding member 372 may have a spring bias to bias the members back to the neutral position. Additionally, expanding member 372 may have a breakaway portion at or proximate pivot 380 that allows either first leg 374 to separate from second leg 376 upon the exertion of a force greater than a predetermined force in vector direction 378. It is also contemplated that expanding member may have a breakaway portion at pivots 380 and/or 832 where expanding member connects to first portion 368 and second portion 370 respectively.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The features described herein may be combined in any combination and such combinations are contemplated. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A robotic catheter system comprising:
a connector defining a pathway and including a first connection member, a second connection member and a breakaway portion, the breakaway portion being at a center portion of the connector, the center portion being at a separate location than the first connection member and the second connection member,
the connector including a region of alternating ridges and grooves proximate the first connection member;
a catheter extending through the connector, wherein the first connection member and the second connection member separable at the breakaway portion once a predetermined force is applied to the connector.

2. The robotic catheter system of claim 1, wherein the breakaway portion is a friction connection.

3. The robotic catheter system of claim 1, wherein the connector is coupled to a track with another portion of the robotic catheter system.

4. The robotic catheter system of claim 3, wherein the connector is coupled to the track and an introducer.

5. The robotic catheter system of claim 4, wherein the catheter extends through the introducer and the track.

6. The robotic catheter system of claim 4, wherein the ridges and grooves form accordion folds that collapse or expand to permit the connector to have a greater or lesser distance between the track and the introducer.

7. The robotic catheter system of claim 1, wherein the connector moves upon a predetermined compressive force applied to a distal end and a proximal end of the connector.

8. The robotic catheter system of claim 1, wherein the connector buckles upon a predetermined compressive force applied to a distal end and a proximal end of the connector.

9. A robotic catheter system comprising:
a drive, operatively moving a catheter along a longitudinal axis;
a connector including,
a folding portion allowing a body to become longer and shorter along the longitudinal axis, the body defining a pathway,
a breakaway connection, the breakaway connection being at a center portion of the connector, the center portion being at a separate location than a first portion of the connector and a second portion of the connector, the breakaway connection permitting a first portion of the connector and the second portion of the connector to move at least one of toward or away from each other; and
the catheter extending through the pathway.

10. The robotic catheter system of claim 9, wherein the body provides a pathway for the catheter to extend therethrough such that the body prevents buckling of the catheter.

11. The robotic catheter system of claim 9, wherein the folding portion extends between a track and an introducer.

12. The robotic catheter system of claim 9, wherein the connector includes a pivot.

13. The robotic catheter system of claim 12, wherein the connector couples a track with another portion of the robotic catheter system.

14. The robotic catheter system of claim 9, wherein the connector couples a track with another portion of the robotic catheter system.

* * * * *